US012653408B2

(12) United States Patent
Fujimoto

(10) Patent No.: US 12,653,408 B2
(45) Date of Patent: Jun. 16, 2026

(54) HEART RATE MEASUREMENT SYSTEM, HEART RATE MEASUREMENT METHOD, AND PROGRAM

(71) Applicant: Sony Group Corporation, Tokyo (JP)

(72) Inventor: Takashi Fujimoto, Chiba (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 18/833,920

(22) PCT Filed: Feb. 20, 2023

(86) PCT No.: PCT/JP2023/005921
§ 371 (c)(1),
(2) Date: Jul. 29, 2024

(87) PCT Pub. No.: WO2023/171337
PCT Pub. Date: Sep. 14, 2023

(65) Prior Publication Data
US 2025/0152028 A1    May 15, 2025

(30) Foreign Application Priority Data

Mar. 11, 2022    (JP) ................................ 2022-038012

(51) Int. Cl.
*A61B 5/024* (2006.01)
*A61B 5/00* (2006.01)
(52) U.S. Cl.
CPC ........ *A61B 5/02416* (2013.01); *A61B 5/7203* (2013.01); *A61B 5/7485* (2013.01); *A61B 2576/02* (2013.01)
(58) Field of Classification Search
CPC . A61B 5/02416; A61B 5/7203; A61B 5/7485; A61B 2576/02; A61B 5/02;
(Continued)

(56) References Cited

U.S. PATENT DOCUMENTS

| | | | | |
|---|---|---|---|---|
| 7,218,759 B1 * | 5/2007 | Ho | ....................... | G06V 40/162 |
| | | | | 382/199 |
| 7,352,880 B2 * | 4/2008 | Kim | .................... | G06V 40/161 |
| | | | | 382/103 |

(Continued)

FOREIGN PATENT DOCUMENTS

| | | | | | |
|---|---|---|---|---|---|
| JP | 2014505533 A | * | 3/2014 | ........... | A61B 5/1122 |
| JP | 2014-221172 A | | 11/2014 | | |

(Continued)

OTHER PUBLICATIONS

Verkruysse [Remote plethysmographic imaging using ambient light, Opt Express. Dec. 22, 2008; 16(26): 21434-21445] (Year: 2008).*

(Continued)

*Primary Examiner* — Oommen Jacob
(74) *Attorney, Agent, or Firm* — Paratus Law Group, PLLC

(57)    ABSTRACT

There is provided a heart rate measurement system, a heart rate measurement method, and a program that enable more accurate heart rate measurement to be performed stably. Ambient light information is acquired from a moving image obtained by imaging a subject with light for each of at least three or more of a plurality of wavelength ranges, the ambient light information including at least a luminance intensity for each wavelength range of ambient light in which the moving image is captured. Further, an ambient light map in which reference ambient light information, which is the ambient light information obtained by measuring ambient light at a plurality of imaging points in advance, is registered for each of the imaging points is referred to, and a desired wavelength is selected on the basis of the ambient light information at an imaging point at which the moving image is captured. Then, a heart rate of the subject shown in the moving image is calculated on the basis of the selected (Continued)

wavelength. The present technology can be applied to, for example, a heart rate measurement system.

10 Claims, 7 Drawing Sheets

(58) Field of Classification Search
CPC ... A61B 5/1176; A61B 5/0077; A61B 5/0245; A61B 5/1171; H04N 23/50
See application file for complete search history.

(56) References Cited

U.S. PATENT DOCUMENTS

| | | | | | |
|---|---|---|---|---|---|
| 7,859,595 | B2* | 12/2010 | Gutta | | H04N 9/73 |
| | | | | | 348/832 |
| 8,055,067 | B2* | 11/2011 | Petrescu | | G06V 40/162 |
| | | | | | 382/164 |
| 8,977,347 | B2* | 3/2015 | Mestha | | A61B 5/02405 |
| | | | | | 600/479 |
| 9,659,229 | B2* | 5/2017 | Clifton | | A61B 5/0205 |
| 10,398,353 | B2* | 9/2019 | Addison | | A61B 5/1032 |
| 10,702,188 | B2* | 7/2020 | Addison | | A61B 5/1032 |
| 11,350,850 | B2* | 6/2022 | Jacquel | | A61B 5/1032 |
| 11,446,514 | B2* | 9/2022 | Bahmani | | A61N 5/0622 |
| 12,042,306 | B2* | 7/2024 | Senegas | | A61B 5/7292 |
| 2002/0135677 | A1* | 9/2002 | Noro | | H04N 7/181 |
| | | | | | 348/E7.086 |
| 2009/0202236 | A1* | 8/2009 | Hama | | H04N 23/74 |
| | | | | | 396/155 |
| 2011/0149067 | A1* | 6/2011 | Lewis | | B64D 45/00 |
| | | | | | 348/135 |
| 2014/0135598 | A1* | 5/2014 | Weidl | | A61B 5/48 |
| | | | | | 600/300 |
| 2014/0303454 | A1* | 10/2014 | Clifton | | A61B 5/1176 |
| | | | | | 600/479 |
| 2015/0230750 | A1* | 8/2015 | McDarby | | A61B 5/0507 |
| 2015/0282724 | A1* | 10/2015 | McDuff | | A61B 5/02427 |
| | | | | | 600/479 |
| 2016/0066835 | A1* | 3/2016 | He | | A63B 24/0087 |
| | | | | | 482/4 |
| 2016/0278644 | A1* | 9/2016 | He | | A61B 5/7275 |
| 2017/0014040 | A1* | 1/2017 | Shim | | A61B 5/02438 |
| 2017/0354334 | A1* | 12/2017 | Tarassenko | | A61B 5/742 |
| 2017/0367580 | A1* | 12/2017 | DiMaio | | A61B 5/445 |
| 2018/0140255 | A1* | 5/2018 | Tao | | A61B 5/004 |
| 2019/0082972 | A1* | 3/2019 | Tao | | A61B 5/1102 |
| 2019/0125249 | A1* | 5/2019 | Rattner | | A61B 5/0077 |
| 2020/0138380 | A1* | 5/2020 | Gu | | A61B 5/7207 |
| 2020/0359922 | A1* | 11/2020 | Genicot | | A61B 5/0245 |
| 2021/0153744 | A1* | 5/2021 | Pierro | | A61B 5/14551 |
| 2021/0369117 | A1* | 12/2021 | Lawrence | | A61B 5/6898 |
| 2022/0240783 | A1* | 8/2022 | Fan | | A61B 5/441 |
| 2022/0400989 | A1* | 12/2022 | Myers | | A61B 5/14551 |
| 2023/0218240 | A1* | 7/2023 | Sohn | | A61B 5/0004 |
| 2024/0032810 | A1* | 2/2024 | Verkruijsse | | A61B 5/02427 |
| 2025/0152028 | A1* | 5/2025 | Fujimoto | | A61B 5/7203 |
| 2025/0182431 | A1* | 6/2025 | Miura | | G06V 10/98 |
| 2025/0241535 | A1* | 7/2025 | Filimonov | | A61B 5/0075 |

FOREIGN PATENT DOCUMENTS

| | | |
|---|---|---|
| JP | 2018-164587 A | 10/2018 |
| JP | 2019-080811 A | 5/2019 |
| JP | 2020-162871 A | 10/2020 |
| JP | 2021-019940 A | 2/2021 |

OTHER PUBLICATIONS

Ernst [Optimal color channel combination across skin tones for remote heart rate measurement in camera-based photoplethysmography, Biomedical Signal Processing and Control 68 (2021) 102644] (Year: 2021).*

Kwon [ROI analysis for remote photoplethysmography on facial video, 2015 IEEE] (Year: 2015).*

Corral [Optimal wavelength selection for non-contact reflection photoplethysmography, Proc. of SPIE vol. 8011, 801191 2011 SPIE] (Year: 2011).*

* cited by examiner

FIG. 2

| POINT | WAVELENGTH (nm) | TIME | | | | | |
|---|---|---|---|---|---|---|---|
| | | 6~9 | 9~12 | 12~15 | 15~18 | 18~21 | |
| A | 400~450 | 1 | 1 | 1 | 1 | 1 | LUMINANCE INTENSITY |
| | 450~500 | 2 | 2 | 2 | 2 | 1 | |
| | 500~550 | 4 | 4 | 4 | 4 | 2 | |
| | 550~600 | 6 | 6 | 9 | 7 | 3 | |
| | 600~650 | 6 | 6 | 8 | 7 | 2 | |
| | 650~700 | 4 | 7 | 8 | 6 | 2 | |
| | 700~750 | 3 | 4 | 5 | 4 | 3 | |
| | 750~800 | 2 | 3 | 2 | 3 | 2 | |

| POINT | WAVELENGTH (nm) | TIME | | | | | |
|---|---|---|---|---|---|---|---|
| | | 6~9 | 9~12 | 12~15 | 15~18 | 18~21 | |
| B | 400~450 | 2 | 2 | 2 | 2 | 2 | LUMINANCE INTENSITY |
| | 450~500 | 2 | 2 | 2 | 2 | 2 | |
| | 500~550 | 4 | 4 | 4 | 12 | 2 | |
| | 550~600 | 6 | 7 | 10 | 10 | 4 | |
| | 600~650 | 6 | 7 | 9 | 9 | 4 | |
| | 650~700 | 4 | 7 | 8 | 7 | 3 | |
| | 700~750 | 3 | 5 | 5 | 4 | 3 | |
| | 750~800 | 2 | 4 | 3 | 4 | 2 | |

FIG. 6

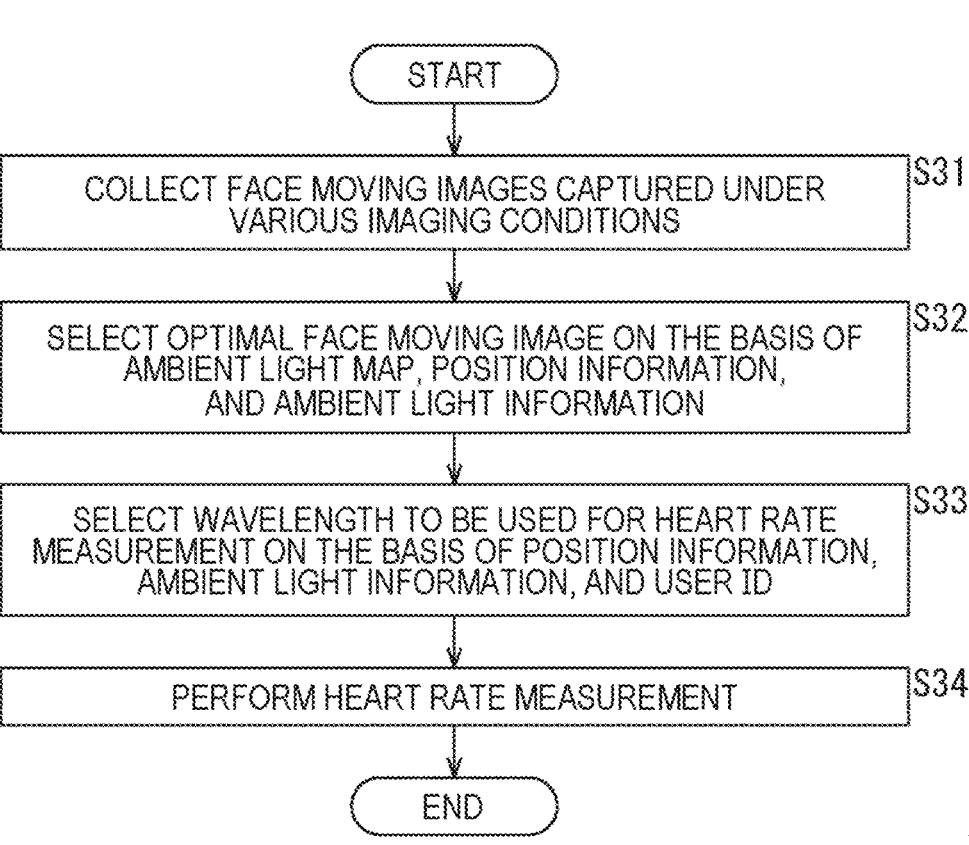

START

COLLECT FACE MOVING IMAGES CAPTURED UNDER VARIOUS IMAGING CONDITIONS | S31

SELECT OPTIMAL FACE MOVING IMAGE ON THE BASIS OF AMBIENT LIGHT MAP, POSITION INFORMATION, AND AMBIENT LIGHT INFORMATION | S32

SELECT WAVELENGTH TO BE USED FOR HEART RATE MEASUREMENT ON THE BASIS OF POSITION INFORMATION, AMBIENT LIGHT INFORMATION, AND USER ID | S33

PERFORM HEART RATE MEASUREMENT | S34

END

FIG. 7

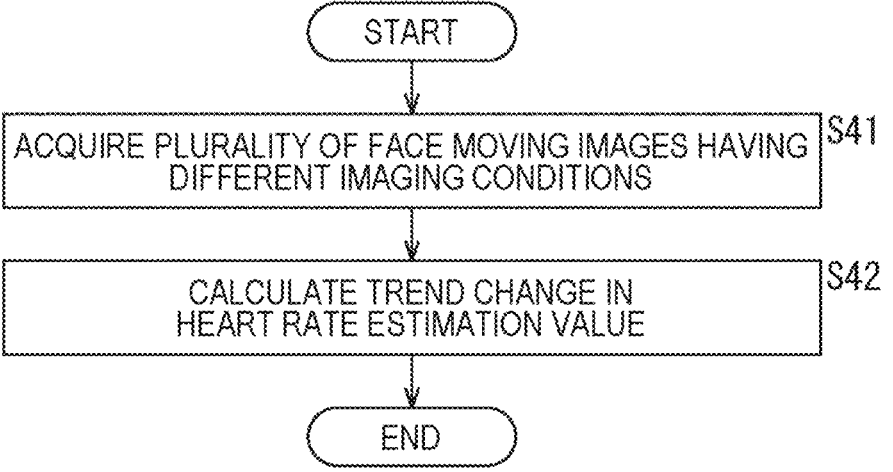

START

ACQUIRE PLURALITY OF FACE MOVING IMAGES HAVING DIFFERENT IMAGING CONDITIONS | S41

CALCULATE TREND CHANGE IN HEART RATE ESTIMATION VALUE | S42

END

*FIG. 9*

HEART RATE MEASUREMENT SYSTEM, HEART RATE MEASUREMENT METHOD, AND PROGRAM

CROSS REFERENCE TO PRIOR APPLICATION

This application is a National Stage Patent Application of PCT International Patent Application No. PCT/JP2023/005921 (filed on Feb. 20, 2023) under 35 U.S.C. § 371, which claims priority to Japanese Patent Application No. 2022-038012 (filed on Mar. 11, 2022), which are all hereby incorporated by reference in their entirety.

TECHNICAL FIELD

The present disclosure relates to a heart rate measurement system, a heart rate measurement method, and a program, and more particularly, to a heart rate measurement system, a heart rate measurement method, and a program capable of stably performing more accurate heart rate measurement.

BACKGROUND ART

In the related art, a technique of obtaining a heart rate through calculation by performing image analysis on a moving image in which a face is imaged has been developed.

For example, Patent Document 1 discloses a pulse wave detection device that extracts a component of a frequency band in which pulse waves can be taken from a luminance signal representing each pixel included in a living body region, and controls whether or not to execute detection of the pulse waves from the luminance signal of the living body region from which the component of the frequency band has been extracted, using luminance information related to display of a screen.

In addition, Patent Document 2 discloses a pulse wave detection device that derives pulse wave information from pixel values acquired from each of a plurality of partial regions on the basis of a reliability associated with each of the plurality of partial regions of a face of a subject in a moving image, and outputs the pulse wave information.

CITATION LIST

Patent Document

Patent Document 1: Japanese Patent Application Laid-Open No. 2014-221172
Patent Document 2: Japanese Patent Application Laid-Open No. 2018-164587

SUMMARY OF THE INVENTION

Problems to be Solved by the Invention

Meanwhile, in the related art, heart rate measurement using reflected light from a face is performed mainly using ambient light as a light source. However, for example, since ambient light greatly changes depending on a date and time, a location, and the like, it is difficult to stably perform accurate heart rate measurement by excluding the influence of such ambient light.

The present disclosure has been made in view of such a circumstance, and is intended to enable more accurate heart rate measurement to be performed stably.

Solutions to Problems

A heart rate measurement system according to one aspect of the present disclosure includes: an ambient light preprocessing unit configured to acquire ambient light information from a moving image obtained by imaging a subject with light for each of at least three or more of a plurality of wavelength ranges, the ambient light information including at least a luminance intensity for each wavelength range of ambient light in which the moving image is captured; a wavelength selection unit configured to refer to an ambient light map in which reference ambient light information, which is the ambient light information obtained by measuring ambient light at a plurality of imaging points in advance, is registered for each of the imaging points, and select a desired wavelength on the basis of the ambient light information at an imaging point at which the moving image is captured; and a heart rate calculation unit configured to calculate a heart rate of the subject shown in the moving image on the basis of the selected wavelength.

A heart rate measurement method or a program according to one aspect of the present disclosure includes: acquiring ambient light information from a moving image obtained by imaging a subject with light for each of at least three or more of a plurality of wavelength ranges, the ambient light information including at least a luminance intensity for each wavelength range of ambient light in which the moving image is captured; referring to an ambient light map in which reference ambient light information, which is the ambient light information obtained by measuring ambient light at a plurality of imaging points in advance, is registered for each of the imaging points, and selecting a desired wavelength on the basis of the ambient light information at an imaging point at which the moving image is captured; and calculating a heart rate of the subject shown in the moving image on the basis of the selected wavelength.

In one aspect of the present disclosure, ambient light information is acquired from a moving image obtained by imaging a subject with light for each of at least three or more of a plurality of wavelength ranges, the ambient light information including at least a luminance intensity for each wavelength range of ambient light in which the moving image is captured, an ambient light map in which reference ambient light information, which is the ambient light information obtained by measuring ambient light at a plurality of imaging points in advance, is registered for each of the imaging points is referred to, and a desired wavelength is selected on the basis of the ambient light information at an imaging point at which the moving image is captured, and a heart rate of the subject shown in the moving image is calculated on the basis of the selected wavelength.

BRIEF DESCRIPTION OF DRAWINGS

FIG. 2 is a diagram illustrating an example of an ambient light map.

FIG. 6 is a flowchart illustrating a processing example of heart rate measurement processing in a third use case.

FIG. 7 is a flowchart illustrating a processing example of heart rate measurement processing in a fourth use case.

FIG. 9 is a block diagram illustrating a configuration example of an embodiment of a computer to which the present technology is applied.

MODE FOR CARRYING OUT THE INVENTION

Hereinafter, specific embodiments to which the present technology is applied will be described in detail with reference to the drawings.

<First Configuration Example of Heart Rate Measurement System>

Figure 1:
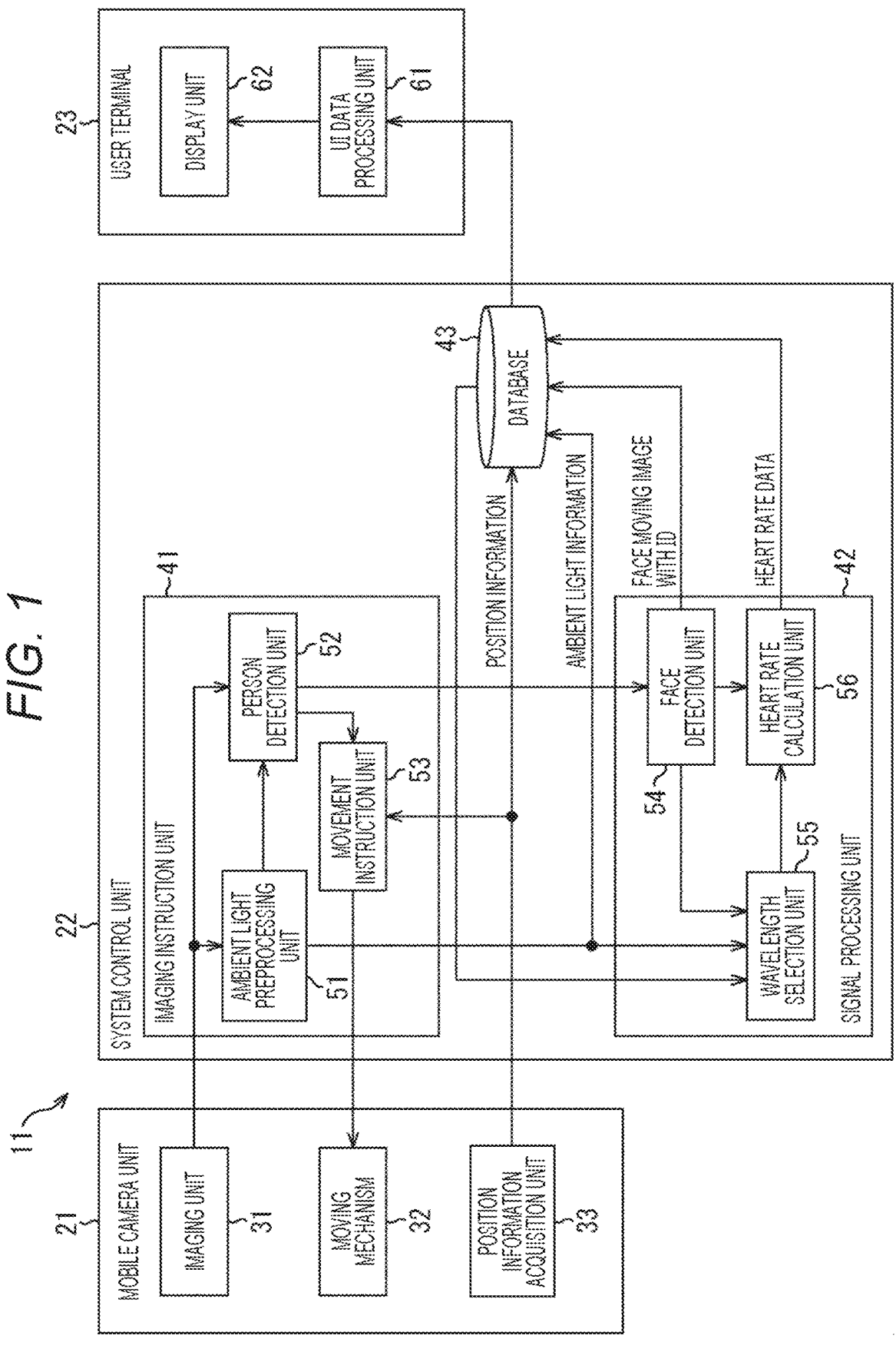
FIG. 1 is a block diagram illustrating a configuration example of a first embodiment of a heart rate measurement system to which the present technology is applied.

FIG. 1 is a block diagram illustrating a configuration example of a first embodiment of a heart rate measurement system to which the present technology is applied.

As illustrated in FIG. 1, a heart rate measurement system 11 includes a mobile camera unit 21, a system control unit 22, and a user terminal 23. For example, the heart rate measurement system 11 can utilize some functions of robots that execute known tasks while moving indoors on a daily basis, such as a pet robot and a cleaning robot, for the mobile camera unit 21, and can be utilized by adding a heart rate measurement function to such robots.

The mobile camera unit 21 includes an imaging unit 31, a moving mechanism 32, and a position information acquisition unit 33.

The imaging unit 31 includes a multispectral camera capable of detecting light for each of a plurality of wavelength ranges larger than three wavelength ranges of red, green, and blue necessary for capturing a general RGB image. Then, the imaging unit 31 captures an image with light for each of at least three or more of a plurality of wavelength ranges to acquire a moving image including pixel data indicating luminance values of the respective wavelength ranges, and supplies the moving image to the system control unit 22.

The moving mechanism 32 is configured by combining legs, tires, motors, and the like, for example, and can move the mobile camera unit 21 to a desired imaging point in accordance with an instruction from the system control unit 22.

As the position information acquisition unit 33, for example, a position sensor used in a function of simultaneously estimating a self position and creating an environmental map, such as simultaneous localization and mapping (SLAM), is used. Then, the position information acquisition unit 33 acquires position information indicating the position of the mobile camera unit 21 and supplies the position information to the system control unit 22.

The system control unit 22 includes an imaging instruction unit 41, a signal processing unit 42, and a storage unit 43.

The imaging instruction unit 41 includes an ambient light preprocessing unit 51, a person detection unit 52, and a movement instruction unit 53.

The ambient light preprocessing unit 51 performs ambient light preprocessing of acquiring ambient light information indicating a luminance intensity for each wavelength range in ambient light in an environment in which a moving image supplied from the imaging unit 31 to the system control unit 22 is captured. Then, the ambient light preprocessing unit 51 supplies the ambient light information acquired by the ambient light preprocessing to the person detection unit 52, a wavelength selection unit 55 of the signal processing unit 42, and the storage unit 43.

When detecting that a person is shown in the moving image supplied from the imaging unit 31 to the system control unit 22, the person detection unit 52 supplies the moving image to a face detection unit 54 of the signal processing unit 42. Furthermore, on the basis of the ambient light information supplied from the ambient light preprocessing unit 51, the person detection unit 52 can specify an imaging point at which the user can be imaged with ambient light more suitable for heart rate measurement with reference to the ambient light map (see FIG. 2), and can notify the movement instruction unit 53 of the imaging point.

The movement instruction unit 53 instructs the moving mechanism 32 to move to the imaging point notified from the person detection unit 52 on the basis of the position information of the mobile camera unit 21 supplied from the position information acquisition unit 33 to the system control unit 22.

The signal processing unit 42 includes the face detection unit 54, the wavelength selection unit 55, and a heart rate calculation unit 56.

The face detection unit 54 performs face detection processing on a person shown in the moving image supplied from the person detection unit 52, detects the face of the person, and acquires a face moving image obtained by cutting out a region in which the face is shown. Furthermore, the face detection unit 54 collates the acquired face moving image with a face image having a user ID registered in advance for each user who is subject in the heart rate measurement system 11, and acquires a user ID for identifying a person in the face moving image. Then, the face detection unit 54 supplies the user ID to the wavelength selection unit 55, supplies the face moving image to the heart rate calculation unit 56, and supplies the face moving image with ID in which the user ID is added to the face moving image to the storage unit 43.

The wavelength selection unit 55 reads the luminance intensity corresponding to the position information of the mobile camera unit 21 supplied from the position information acquisition unit 33 to the storage unit 43 from the ambient light map (see FIG. 2) stored in the storage unit 43. Then, the wavelength selection unit 55 refers to the luminance intensity, selects a desired wavelength on the basis of the ambient light information supplied from the ambient light preprocessing unit 51, and notifies the heart rate calculation unit 56 of the selected wavelength. Note that a method of wavelength selection will be described later with reference to FIG. 2. Furthermore, the wavelength selection unit 55 can select a wavelength suitable for each user identified by the user ID supplied from the face detection unit 54.

Furthermore, the wavelength selection unit 55 can select a face moving image optimal for heart rate measurement from among a plurality of face moving images captured under various imaging conditions (imaging point and imaging time) accumulated in the storage unit 43, and supply the selected face moving image to the heart rate calculation unit 56.

The heart rate calculation unit 56 calculates the heart rate of the user shown in the moving image supplied from the face detection unit 54 on the basis of the wavelength selected by the wavelength selection unit 55. For example, the heart rate calculation unit 56 extracts pixel data including the wavelength notified from the wavelength selection unit 55 among the pixel data for each of the plurality of wavelength ranges constituting the face moving image supplied from the face detection unit 54, and calculates the heart rate using the pixel data. Accordingly, the heart rate calculation unit 56 performs heart rate measurement and supplies heart rate data obtained by the measurement to the storage unit 43.

Furthermore, the heart rate calculation unit 56 can read and acquire a plurality of face moving images with different imaging conditions (imaging point, imaging time, imaging date) for a specific user identified by the user ID from the storage unit 43, calculate the heart rates of the users shown in the face moving images, and calculate a trend change in heart rate estimation value that changes along the time series.

The storage unit 43 stores, in a database, an ambient light map in which the ambient light information supplied from the ambient light preprocessing unit 51 is registered for each piece of the position information supplied from the position information acquisition unit 33. In addition, the storage unit 43 stores the face moving image with ID supplied from the face detection unit 54 and the heart rate data supplied from the heart rate calculation unit 56 in association with each other.

The user terminal 23 includes a UI data processing unit 61 and a display unit 62. For example, a smartphone, a tablet terminal, or the like can be used as the user terminal 23.

The UI data processing unit 61 performs data processing for creating a user interface screen, which will be described later with reference to FIG. 3, on the basis of the ambient light map stored in the storage unit 43, for example, and supplies the created user interface screen to the display unit 62.

The display unit 62 displays the user interface screen created by the UI data processing unit 61.

The heart rate measurement system 11 configured as described above can refer to the ambient light map obtained by the measurement in advance on the basis of the ambient light information acquired by the ambient light preprocessing unit 51, and select the wavelength optimal for performing the heart rate measurement at the imaging point where the face moving image is captured. Accordingly, the heart rate measurement system 11 can reduce the influence of ambient light and can stably perform more accurate heart rate measurement. For example, the ambient light map is obtained by analyzing an indoor floor plan where the heart rate measurement is performed by the heart rate measurement system 11, detecting an ambient light robust place, and preliminarily capturing and accumulating a relationship between the ambient light and the imaging point.

Furthermore, the heart rate measurement system 11 can capture a face moving image by moving the mobile camera unit 21 to an imaging point where the user can be imaged with ambient light more suitable for heart rate measurement, the imaging point being specified by referring to the ambient light map. In addition, the heart rate measurement system 11 can present an imaging time with which the user can be imaged with ambient light more suitable for heart rate measurement, for example, by storing an illumination fluctuation pattern within a day at each imaging place.

For example, the heart rate measurement system 11 can utilize some functions of robots that execute known tasks while moving indoors on a daily basis, such as pet robots, cleaning robots, and the like, for the mobile camera unit 21, to use the indoor floor plan that such robots have already detected with SLAM. For example, a heart rate measurement function can be added to the robot as one of functions of monitoring health of a family.

Then, the heart rate measurement system 11 may use, as the ambient light information, a color temperature obtained by detecting indoor illuminance, a type of illumination, and the like for each season. Accordingly, it may be estimated under illumination of what color temperature the face facing in a certain direction at a certain place at a certain time. In addition, the heart rate measurement system 11 can select an optimal spectrum for extracting the heart rate from the skin color when capturing the face moving image based on the color temperature estimation, and can be expected to improve the S/N quality of the heart rate estimation. The heart rate measurement system 11 can also identify users using the face detection unit 54 and select a wavelength suitable for each user.

With reference to the ambient light map illustrated in FIG. 2, a method of handling ambient light and selecting a wavelength in the heart rate measurement system 11 will be described.

FIG. 2 illustrates an example of the ambient light map in which the luminance intensity for each time slot and wavelength range is registered in association with two indoor imaging points A and B. In the illustrated example, there are values of the luminance intensity for every eight wavelength ranges (400-450, 450-500, 500-550, 550-600, 600-650, 650-700, 700-750, 750-800) in increments of 50 nm in five time slots (6:00-9:00, 9:00-12:00, 12:00-15:00, 15:00-18:00, 18:00-21:00). Note that the values of the luminance intensity illustrated in FIG. 2 are provisional values for describing the processing in the heart rate measurement system 11, and for example, values in various expressions such as values such as a weekly average and a monthly average, and values collected according to the influence of external light such as weather may be used.

The heart rate measurement system 11 acquires such luminance intensity data through measurement in advance, and stores the luminance intensity data in the storage unit 43. Then, the heart rate measurement system 11 can acquire the luminance intensity for each wavelength expected at the imaging point and the imaging time by specifying the imaging point and the imaging time indoors. That is, the heart rate measurement system 11 can acquire the value of the luminance intensity for each wavelength range expected to be the base of the ambient light in the user's face moving image captured for performing the heart rate measurement. Accordingly, by performing processing such as dividing the signal of each wavelength of the heartbeat component using the value, the wavelength component can be leveled and averaged, and the S/N of the heartbeat component included in each wavelength component is expected to be improved.

Then, the heartbeat component obtained from the face moving image is expected to have a different optimal wavelength as a source of extraction depending on the environment, a person, or the like. Therefore, by specifying the face moving image captured at which point and at which time as in the heart rate measurement system 11, it becomes an index of which wavelength range component is preferably used to extract the heartbeat component, and the wavelength range can be easily selected.

For example, it is assumed that a face moving image is captured in the time slot from 12:00 to 15:00 at the imaging point A. At this time, as the ambient light, the value of the luminance intensity in the wavelength range from 550 nm to 700 nm is high, and in particular, the value of the luminance intensity in the wavelength range from 550 nm to 600 nm is high. Therefore, probabilistically, it can be expected that a component excellent in terms of S/N is extracted from the wavelength range of 550-600 nm among the heartbeat components hidden in each wavelength range of the face moving image. In this way, it is possible to select a wavelength range in which the heartbeat component is obtained using the luminance intensity of the ambient light as a parameter.

In addition, after selecting a wavelength and measuring heart rate, the quality of the measurement results can be ranked and linked to location and time, so that it is possible to specify an imaging point and an imaging time which are convenient for the heart rate measurement.

Furthermore, in a case where the imaging point and the imaging time can be selected, the user can be guided to the optimal imaging point and imaging time on the basis of the imaging point and the imaging time at which the luminance intensity and the quality of the measurement results up to the previous time are good. For example, as illustrated in FIG. 2, it is assumed that an image is captured somewhere in a time slot from 12:00 to 15:00 using a wavelength range from 550 nm to 700 nm at the imaging point A. In this case, if the imaging point and the imaging time are selected, there is a possibility that the quality of the measurement result of the face heart rate is higher when imaging is performed using the wavelength range from 500 nm to 650 nm of the imaging point B. Therefore, it is preferable to guide the user to the imaging point B at that time and perform imaging.

Figure 3:
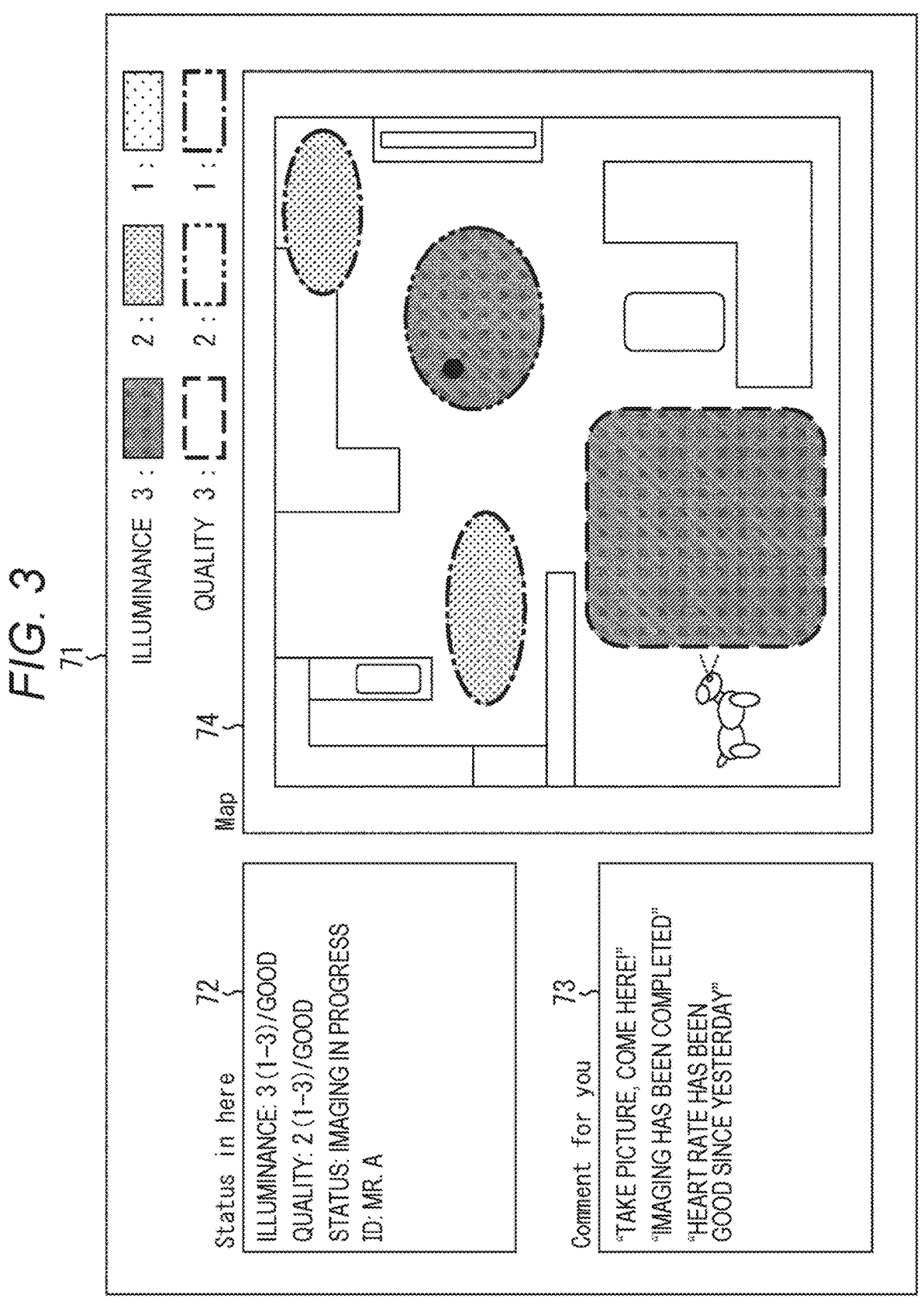
FIG. 3 is a diagram illustrating an example of a user interface screen.

FIG. 3 illustrates an example of a user interface screen displayed on the display unit 62 of the user terminal 23.

A user interface screen 71 illustrated in FIG. 3 is provided with a status display unit 72, a comment display unit 73, and a map display unit 74.

The status display unit 72 displays illuminance at the current position of the mobile camera unit 21, quality of heart rate data that can be expected to be obtained when the user's face is imaged at the current position of the mobile camera unit 21, a status indicating whether or not imaging is being performed, and a user name associated with the user ID. In the example illustrated in FIG. 3, it is indicated that the level of illuminance among the three levels is 3, which is good, the level of quality among the three levels is 2, which is good, imaging is in progress, and the user name is Mr. A.

On the comment display unit 73, a comment for encouraging imaging, a message from the heart rate measurement system 11, an announcement regarding the current heart rate measurement value from the past data, and the like are displayed. In the example illustrated in FIG. 3, a comment "Take a picture, come here!", a message "Imaging has been completed", and an announcement "Heart rate has been good since yesterday" are displayed.

In the map display unit 74, for example, an indoor map created by the SLAM of the mobile camera unit 21 is displayed, and regions according to the level of the illuminance and the quality of the heart rate data in the map are represented according to a color (hatching in the illustrated example) and a type of a frame line. Furthermore, the map display unit 74 can display the current position of the mobile camera unit 21, and can guide the user to the place to capture an image.

<Processing Example of Heart Rate Measurement Processing>

Processing examples of heart rate measurement processing in first to fourth use cases will be described with reference to FIGS. 4 to 7.

Figure 4:
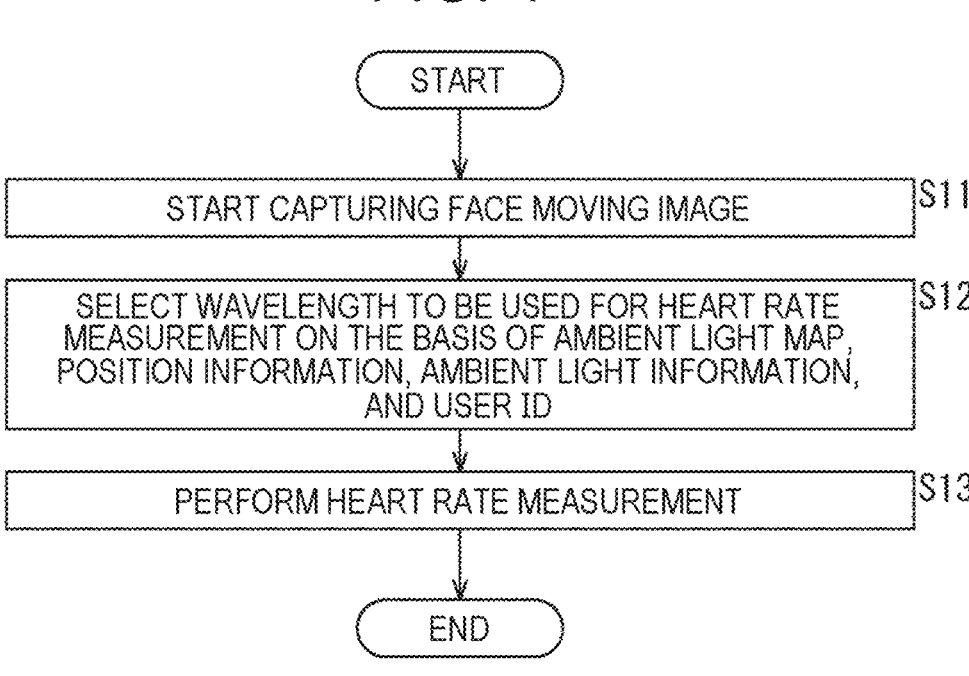
FIG. 4 is a flowchart illustrating a processing example of heart rate measurement processing in a first use case.

FIG. 4 is a flowchart illustrating a processing example of heart rate measurement processing in the first use case.

In step S11, if the moving image captured by the imaging unit 31 is supplied to the person detection unit 52 and it is detected that a person is shown in the moving image, the supply of the moving image from the person detection unit 52 to the face detection unit 54 is started. Then, the face detection unit 54 acquires a face moving image by cutting out a region in which the face is shown in the moving image, and supplies the face moving image to the heart rate calculation unit 56.

In step S12, the wavelength selection unit 55 selects a wavelength to be used for heart rate measurement on the basis of the ambient light map stored in the storage unit 43, the position information of the mobile camera unit 21 acquired by the position information acquisition unit 33, the ambient light information supplied from the ambient light preprocessing unit 51, and the user ID supplied from the face detection unit 54, and notifies the heart rate calculation unit 56 of the selected wavelength.

In step S13, the heart rate calculation unit 56 calculates the heart rate of the user shown in the face moving image supplied from the face detection unit 54 in step S11 on the basis of the wavelength notified from the wavelength selection unit 55 in step S12, and performs heart rate measurement.

In this way, in the first use case, the heart rate measurement system 11 can reduce the influence of the ambient light and stably perform more accurate heart rate measurement by selecting the wavelength optimal for performing the heart rate measurement at the imaging point where the face moving image is captured.

Figure 5:
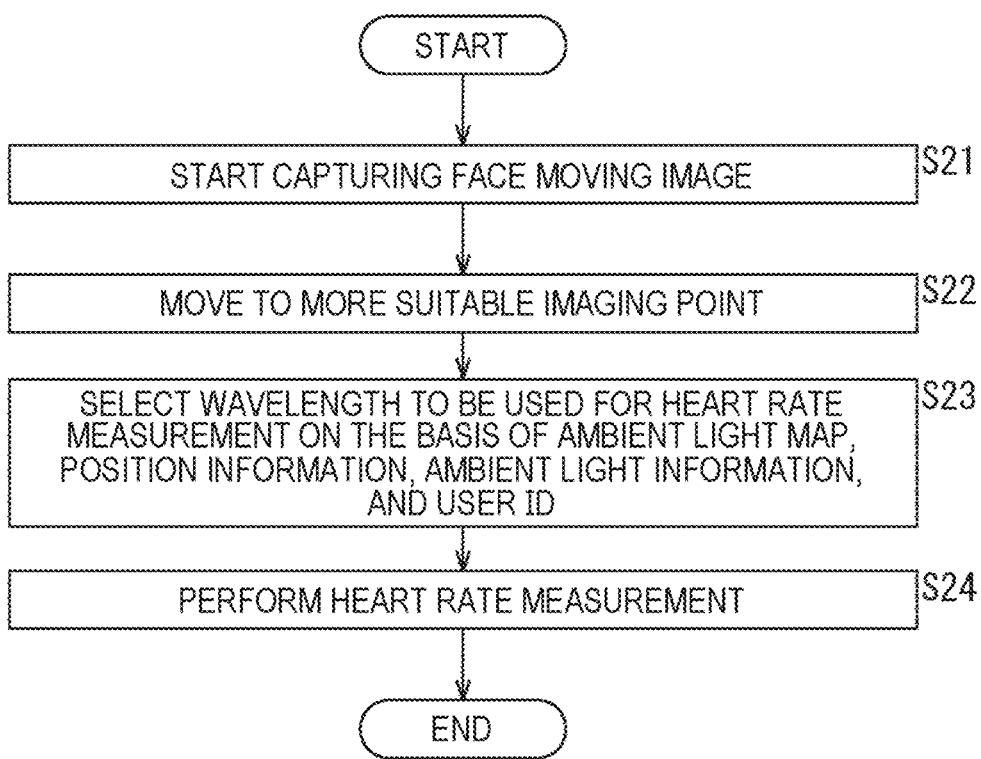
FIG. 5 is a flowchart illustrating a processing example of heart rate measurement processing in a second use case.

FIG. 5 is a flowchart illustrating a processing example of heart rate measurement processing in the second use case.

In step S21, similarly to step S11 in FIG. 4, capturing of the face moving image is started.

In step S22, on the basis of the ambient light information supplied from the ambient light preprocessing unit 51, the person detection unit 52 specifies an imaging point at which the person can be imaged with ambient light more suitable for heart rate measurement with reference to the ambient light map (see FIG. 2), and notifies the movement instruction unit 53 of the imaging point. In response to this, the movement instruction unit 53 instructs the moving mechanism 32 to move. Then, if the mobile camera unit 21 moves to the imaging point instructed by the movement instruction unit 53, the processing proceeds to step S23.

In steps S23 and S24, similarly to steps S12 and S13 in FIG. 4, a wavelength used for heart rate measurement is selected, and heart rate measurement is performed on the basis of the wavelength.

In this way, in the second use case, the heart rate measurement system 11 can further reduce the influence of the ambient light and stably perform more accurate heart rate measurement by moving the mobile camera unit 21 to the imaging point where the person can be imaged with the ambient light more suitable for the heart rate measurement, and then selecting the wavelength optimal for performing the heart rate measurement.

FIG. 6 is a flowchart illustrating a processing example of heart rate measurement processing in the third use case.

In step S31, face moving images captured under various imaging conditions (imaging point and imaging time) are collected and accumulated in the storage unit 43.

In step S32, the wavelength selection unit 55 selects a face moving image optimal for performing heart rate measurement from among a plurality of face moving images accumulated in the storage unit 43 on the basis of the ambient light map stored in the storage unit 43, the position information of the mobile camera unit 21 acquired by the position information acquisition unit 33, and the ambient light information supplied from the ambient light preprocessing unit 51, and supplies the selected face moving image to the heart rate calculation unit 56.

In step S33, the wavelength selection unit 55 selects a wavelength to be used for heart rate measurement on the basis of the position information of the mobile camera unit 21 acquired by the position information acquisition unit 33, the ambient light information supplied from the ambient light preprocessing unit 51, and the user ID supplied from the face detection unit 54, and notifies the heart rate calculation unit 56 of the selected wavelength.

In step S34, the heart rate calculation unit 56 calculates the heart rate of the user shown in the face moving image supplied from the wavelength selection unit 55 in step S32 on the basis of the wavelength notified from the wavelength selection unit 55 in step S33, and performs heart rate measurement.

In this way, in the third use case, the heart rate measurement system 11 can further reduce the influence of the ambient light and stably perform more accurate heart rate measurement by selecting the face moving image optimal for performing the heart rate measurement and selecting the wavelength optimal for performing the heart rate measurement.

FIG. 7 is a flowchart illustrating a processing example of heart rate measurement processing in the fourth use case.

In step S41, the heart rate calculation unit 56 reads and acquires a plurality of face moving images with different imaging conditions (imaging point, imaging time, imaging date) for a specific user identified by the user ID from the storage unit 43.

In step S42, the heart rate calculation unit 56 calculates the heart rate of the user shown in the plurality of face moving images acquired in step S41, and calculates a trend change in heart rate estimation value that changes along the time series.

In this way, in the fourth use case, the heart rate measurement system 11 can catch a change by observing a tendency of heart rates obtained from a plurality of face moving images affected by different ambient light beams. Accordingly, for example, it is possible to extract a parameter used for predicting the deterioration of the health condition and display an announcement of "Heart rate has been good since yesterday" as illustrated in the comment display unit 73 of FIG. 3.

<Second Configuration Example of Heart Rate Measurement System>

Figure 8:
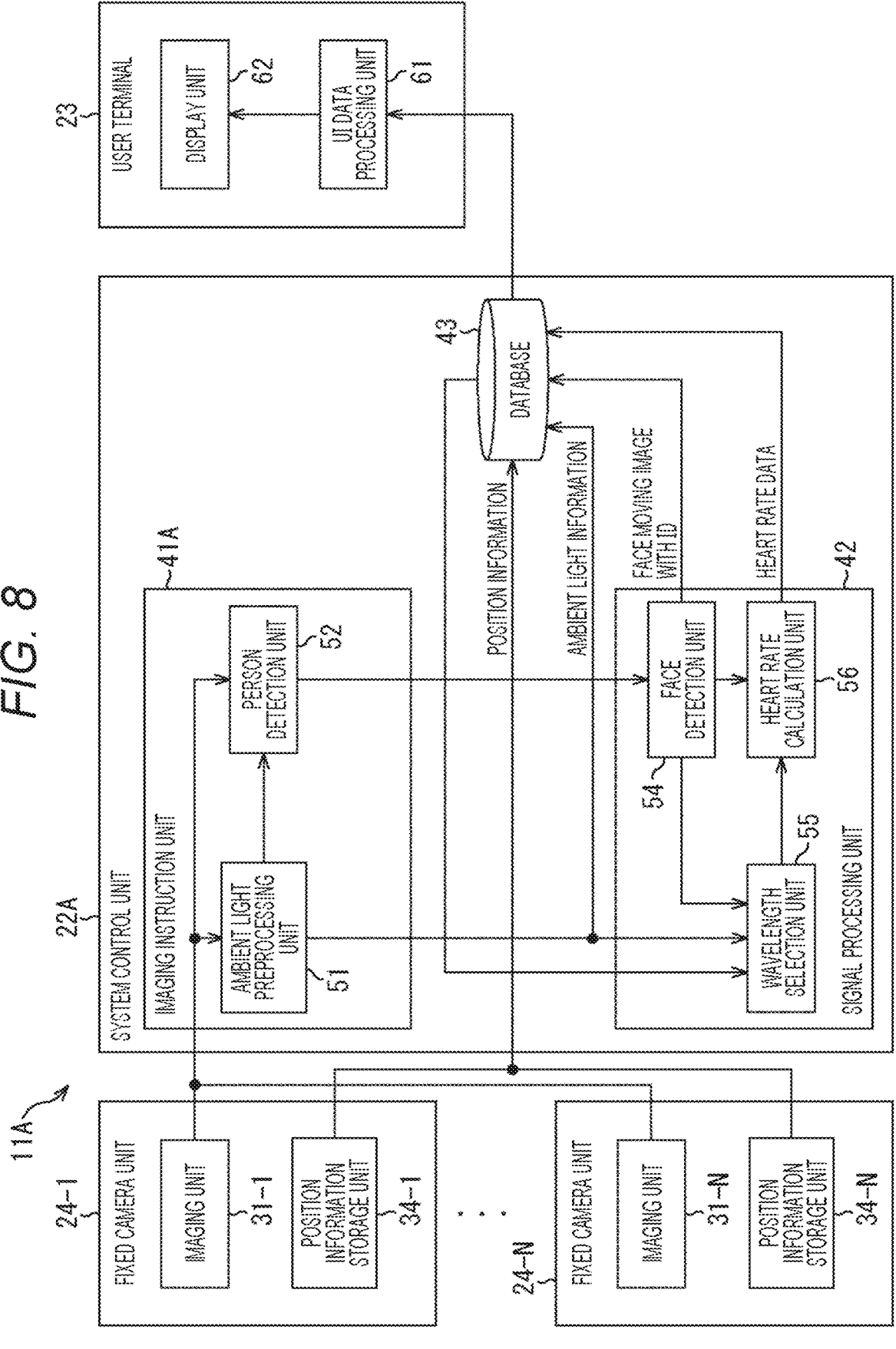
FIG. 8 is a block diagram illustrating a configuration example of a second embodiment of a heart rate measurement system to which the present technology is applied.

FIG. 8 is a block diagram illustrating a configuration example of a second embodiment of a heart rate measurement system to which the present technology is applied. Note that, in a heart rate measurement system 11A illustrated in FIG. 8, the same reference numerals are given to each block common to the configuration of the heart rate measurement system 11 illustrated in FIG. 1, and the detailed description thereof will be omitted.

As illustrated in FIG. 8, the heart rate measurement system 11A includes N fixed camera units 24-1 to 24-N, a system control unit 22A, and a user terminal 23. Note that the fixed camera units 24-1 to 24-N are similarly configured, and will be simply referred to as a fixed camera unit 24 in a case where it is not necessary to distinguish them.

That is, while the heart rate measurement system 11 in FIG. 1 includes the mobile camera unit 21 capable of moving a plurality of imaging points, the heart rate measurement system 11A is configured such that the fixed camera unit 24 is fixedly disposed at each of the plurality of imaging points.

The fixed camera unit 24 includes an imaging unit 31 and a position information storage unit 34.

Similarly to the mobile camera unit 21 in FIG. 1, the imaging unit 31 includes a multispectral camera, and can acquire a moving image captured with light for each of at least three or more of a plurality of wavelength ranges.

The position information storage unit 34 stores position information indicating a fixed position of the fixed camera unit 24 when the fixed camera unit 24 is fixed.

The system control unit 22A includes an imaging instruction unit 41A, a signal processing unit 42, and a storage unit 43, and the signal processing unit 42 and the storage unit 43 have the configuration similar to the signal processing unit 42 and the storage unit 43 of the imaging instruction unit 41 in FIG. 1. Furthermore, the imaging instruction unit 41A is configured similarly to the imaging instruction unit 41 in FIG. 1 in that it includes an ambient light preprocessing unit 51 and a person detection unit 52.

In the heart rate measurement system 11A configured as described above, it is possible to capture a user's face moving image at N imaging points by the fixed camera units 24-1 to 24-N, and it is possible to reduce the influence of ambient light and to stably perform more accurate heart rate measurement, similarly to the heart rate measurement system 11 in FIG. 1.

<Configuration Example of Computer>

Next, a series of processes (heart rate measurement method) described above can be performed by hardware or by software. In a case where a series of processes is performed by the software, a program configuring the software is installed on a general-purpose computer, and the like.

Figure 9:
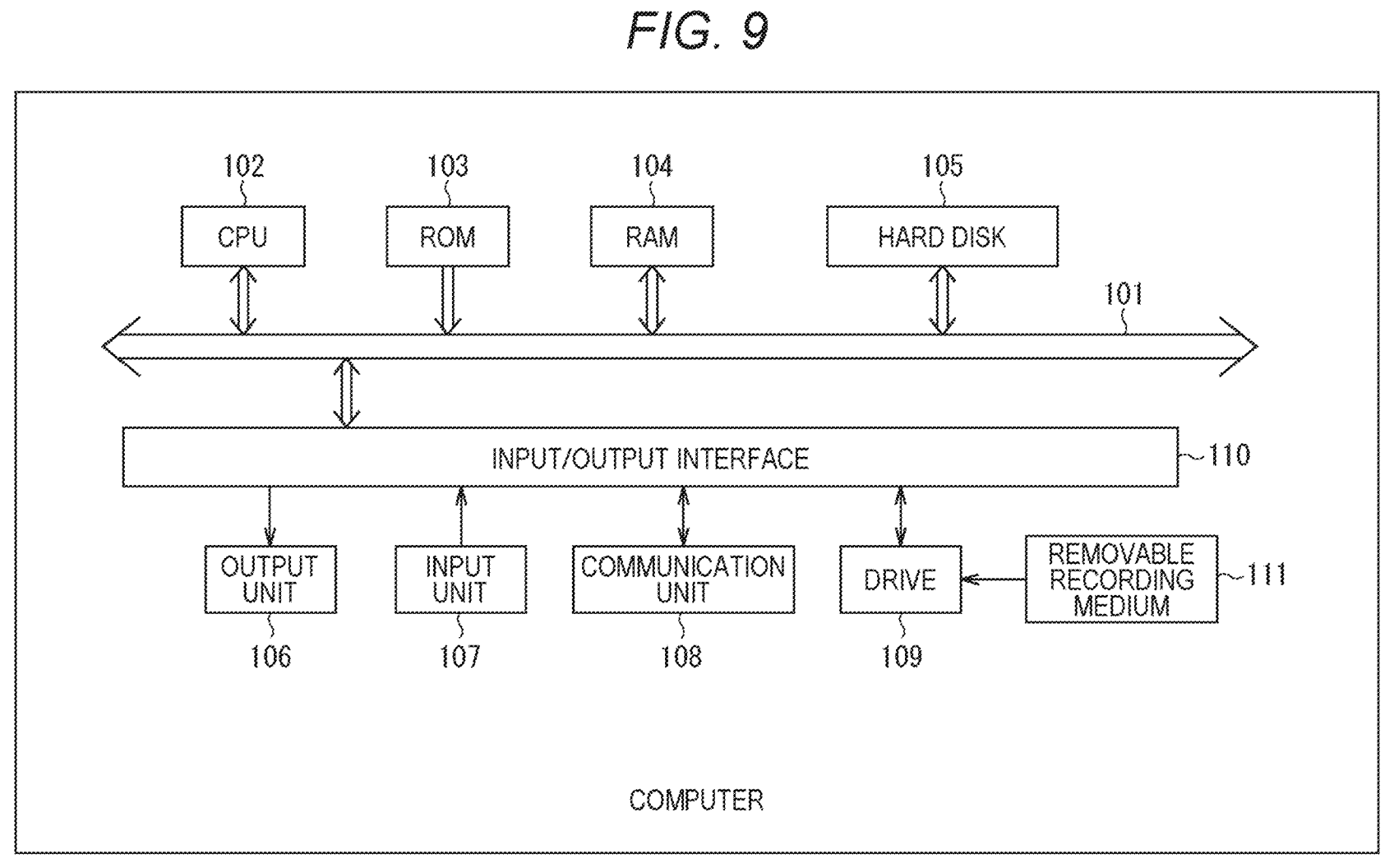

FIG. 9 is a block diagram illustrating a configuration example of an embodiment of a computer on which a program for executing the series of processes described above is installed.

The program can be recorded in advance on a hard disk 105 or a ROM 103 as a recording medium built into the computer.

Alternatively, further, the program can also be stored (recorded) in a removable recording medium 111 driven by a drive 109. Such a removable recording medium 111 can be provided as so-called package software. Here, examples of the removable recording medium 111 include a flexible disk, a compact disc read only memory (CD-ROM), a magneto optical (MO) disk, a digital versatile disc (DVD), a magnetic disk, a semiconductor memory, and the like.

Note that, in addition to installing the program on the computer from the removable recording medium 111 as described above, the program can be downloaded to the computer via a communication network or a broadcasting network and installed on the built-in hard disk 105. In other words, for example, the program can be wirelessly transferred from a download site to the computer via an artificial satellite for digital satellite broadcasting, or can be transferred by wire to the computer via a network such as a local area network (LAN) and the Internet.

The computer has a built-in central processing unit (CPU) 102, and an input/output interface 110 is connected to the CPU 102 via a bus 101.

When a user inputs a command via the input/output interface 110 by operating an input unit 107, the CPU 102 executes a program stored in a read only memory (ROM) 103 in accordance with the command. Alternatively, the CPU 102 loads a program stored in the hard disk 105 into a random access memory (RAM) 104 to execute the program.

Accordingly, the CPU 102 performs processing according to the flowchart described above or processing performed according to the configuration in the block diagram described above. Then, as necessary, the CPU 102 outputs a processing result from an output unit 106, or transmits the processing result from a communication unit 108, and further, causes the hard disk 105 to record the processing result, and the like, via the input/output interface 110, for example.

Note that, the input unit 107 includes a keyboard, a mouse, a microphone, and the like. Furthermore, the output unit 106 includes a liquid crystal display (LCD), a speaker, and the like.

Here, in the present specification, processing that a computer performs in accordance with a program is not necessarily performed in time series according to orders described in the flowcharts. That is, processing that a computer performs in accordance with the program includes processing that is executed in parallel or individually (for example, parallel processing or object-based processing).

Furthermore, the program may be processed by one computer (processor) or processed in a distributed manner by a plurality of computers. Moreover, the program may be transferred to a distant computer and executed.

Moreover, in the present specification, a system means a set of a plurality of components (devices, modules (parts), and the like), and it does not matter whether or not all the components are in the same housing. Therefore, a plurality of devices housed in separate housings and connected via a network and one device in which a plurality of modules is housed in one housing are both systems.

Furthermore, for example, a configuration described as one device (or processing unit) may be divided and configured as the plurality of devices (or processing units). Conversely, configurations described above as a plurality of devices (or processing units) may be collectively configured as one device (or processing unit). Furthermore, it goes without saying that a configuration other than the above-described configurations may be added to the configuration of each device (or each processing unit). Moreover, if the configuration and operation of the entire system are substantially the same, a part of the configuration of a certain device (or processing unit) may be included in the configuration of another device (or another processing unit).

Furthermore, for example, the present technology can be configured as cloud computing in which one function is shared and jointly processed by the plurality of the devices via the network.

Furthermore, for example, the program described above can be executed by any device. In this case, the device is only required to have a necessary function (functional block and the like) and obtain necessary information.

Furthermore, for example, each step described in the flowcharts described above can be executed by one device, or can be executed in a shared manner by the plurality of the devices. Moreover, in a case where a plurality of processing is included in one step, a plurality of the processing included in the one step can be executed by one device or by a plurality of devices in a shared manner. In other words, a plurality of pieces of processing included in one step can be executed as processing of a plurality of steps. Conversely, the processing described as a plurality of steps can be collectively executed as one step.

Note that, in the program to be executed by the computer, the processing of steps describing the program may be executed in time series according to orders described in the present specification, or may be executed in parallel, or independently at a necessary timing such as when a call is made. That is, the processing of each step may be executed in a different order from the order described above, as long as there is no contradiction. Furthermore, the processing of steps describing this program may be executed in parallel with the processing of another program, or may be executed in combination with the processing of another program.

Note that a plurality of the present technologies described in the present specification can be implemented independently as a single body as long as there is no contradiction. Of course, a plurality of arbitrary present technologies can be implemented in combination. For example, some or all of the present technologies described in any of the embodiments can be implemented in combination with some or all of the present technologies described in other embodiments. Furthermore, some or all of the above-described arbitrary present technologies can be implemented in combination with other technologies not described above.

Example of Configuration Combination

Note that the present technology may also have the following configuration.

(1)

A heart rate measurement system including:

an ambient light preprocessing unit configured to acquire ambient light information from a moving image obtained by imaging a subject with light for each of at least three or more of a plurality of wavelength ranges, the ambient light information including at least a luminance intensity for each wavelength range of ambient light in which the moving image is captured;

a wavelength selection unit configured to refer to an ambient light map in which reference ambient light information, which is the ambient light information obtained by measuring ambient light at a plurality of imaging points in advance, is registered for each of the imaging points, and select a desired wavelength on the basis of the ambient light information at an imaging point at which the moving image is captured; and a heart rate calculation unit configured to calculate a heart rate of the subject shown in the moving image on the basis of the selected wavelength.

(2)

The heart rate measurement system according to (1), further including:

a face detection unit configured to detect a face of the subject shown in the moving image, acquire a face moving image obtained by cutting out a region in which the face is shown, and identify the subject by collating the face moving image with a registered face image.

(3)

The heart rate measurement system according to (1) or (2), a camera unit including an imaging unit including a multispectral camera capable of detecting light for each of at least three or more of a plurality of wavelength ranges.

(4)

The heart rate measurement system according to (3), in which the camera unit includes a moving mechanism that is movable to a desired imaging point.

(5)

The heart rate measurement system according to (3), in which a plurality of the camera units is fixedly disposed at a plurality of imaging points, respectively.

(6)

The heart rate measurement system according to (4), further including:

a movement instruction unit configured to instruct the moving mechanism to move to an imaging point where the subject is able to be imaged with ambient light more suitable for heart rate measurement, the ambient light being specified by referring to the ambient light map.

(7)

The heart rate measurement system according to any one of (1) to (6), in which selecting a face moving image optimal for performing a plurality of heart rate measurements captured and accumulated under various imaging conditions is selected, and the heart rate calculation unit calculates a heart rate of the subject shown in the moving image.

(8)

The heart rate measurement system according to any one of (1) to (7), in which the heart rate calculation unit calculates heart rates of the subject shown in a plurality of face moving images with different imaging conditions, and calculates a trend change in heart rate estimation value that changes along a time series of the heart rates.

(9)

A heart rate measurement method performed by a heart rate measurement system, the method including:

acquiring ambient light information from a moving image obtained by imaging a subject with light for each of at least three or more of a plurality of wavelength ranges, the ambient light information including at least a luminance intensity for each wavelength range of ambient light in which the moving image is captured;

referring to an ambient light map in which reference ambient light information, which is the ambient light information obtained by measuring ambient light at a plurality of imaging points in advance, is registered for each of the imaging points, and selecting a desired wavelength on the basis of the ambient light information at an imaging point at which the moving image is captured; and calculating a heart rate of the subject shown in the moving image on the basis of the selected wavelength.

(10)

A program for causing a computer of a heart rate measurement system to execute heart rate measurement processing including:

acquiring ambient light information from a moving image obtained by imaging a subject with light for each of at least three or more of a plurality of wavelength ranges, the ambient light information including at least a luminance intensity for each wavelength range of ambient light in which the moving image is captured;

referring to an ambient light map in which reference ambient light information, which is the ambient light information obtained by measuring ambient light at a plurality of imaging points in advance, is registered for each of the imaging points, and selecting a desired wavelength on the basis of the ambient light information at an imaging point at which the moving image is captured; and calculating a heart rate of the subject shown in the moving image on the basis of the selected wavelength.

Note that, the present embodiment is not limited to the embodiments described above, and various alterations can be made without departing from the gist of the present disclosure. Furthermore, the effects described in the present specification are merely examples and are not limited, and other effects may be provided.

REFERENCE SIGNS LIST

11 Heart rate measurement system
21 Mobile camera unit
22 System control unit
23 User terminal
24-1 to 24-N Fixed camera unit
31 Imaging unit
32 Moving mechanism
33 Position information acquisition unit
34 Position information storage unit
41 Imaging instruction unit
42 Signal processing unit
43 Storage unit
51 Ambient light preprocessing unit
52 Person detection unit
53 Movement instruction unit
54 Face detection unit
55 Wavelength selection unit
56 Heart rate calculation unit
61 UI data processing unit
62 Display unit

The invention claimed is:

1. A heart rate measurement system comprising:

at least one camera configured to detect light; and circuitry configured to acquire light information from a moving image obtained by imaging a subject with light for each wavelength range of at least three wavelength ranges, the light information including at least a luminance intensity for each wavelength range of light in which the moving image is captured, refer to a light map in which reference light information, which is the light information obtained by measuring the light at a plurality of imaging points in advance, is registered for each imaging point of the plurality of imaging points, instruct movement of the at least one camera to a desired imaging point, select a desired wavelength based on of the light information at the desired imaging point at which the moving image is captured, and calculate a heart rate of the subject shown in the moving image based on the selected wavelength.

2. The heart rate measurement system according to claim 1, wherein the circuitry is further configured to detect a face of the subject shown in the moving image, acquire a face region of the moving image obtained by cutting out a region of the moving image in which the face of the subject is shown, and identify the subject by collating the acquired face region of the moving image with a registered face image.

3. The heart rate measurement system according to claim 1, wherein the at least one camera includes a multispectral camera configured to detect the light for each wavelength range of the at least three wavelength ranges.

4. The heart rate measurement system according to claim 3, further comprising:

a moving mechanism configured to move the multispectral camera to the desired imaging point.

5. The heart rate measurement system according to claim 1, wherein the at least one camera includes a plurality of cameras fixedly disposed at the plurality of imaging points.

6. The heart rate measurement system according to claim 4, wherein the circuitry is further configured to instruct the moving mechanism to move to the desired imaging point where the subject is able to be imaged with light more suitable for heart rate measurement, the light being specified by referring to the light map.

7. The heart rate measurement system according to claim 1, wherein a face region of the moving image optimal for performing a plurality of heart rate measurements captured and accumulated under various imaging conditions is selected, and wherein the circuitry calculates the heart rate of the subject shown in the moving image using the selected face region of the moving image.

8. The heart rate measurement system according to claim 1, wherein the circuitry calculates heart rates of the subject shown in a plurality of moving images with different imaging conditions, and wherein the circuitry is further configured to calculate a trend change in heart rate estimation value that changes along a time series of the calculated heart rates.

9. A heart rate measurement method performed by a heart rate measurement system, the method comprising:

acquiring light information from a moving image obtained by imaging a subject using at least one camera with light for each wavelength range of at least three or more of a plurality of wavelength ranges, the light information including at least a luminance intensity for each wavelength range of light in which the moving image is captured;

referring to a light map in which reference light information, which is the light information obtained by measuring light at a plurality of imaging points in advance, is registered for each imaging point of the plurality of imaging points;

instructing movement of the at least one camera to a desired imaging point;

selecting a desired wavelength based on a basis of the light information at the desired imaging point at which the moving image is captured; and calculating a heart rate of the subject shown in the moving image based on the selected wavelength.

10. A non-transitory computer-readable storage medium having embodied thereon a program, which when executed by a computer of a heart rate measurement system causes the computer to execute a heart rate measurement processing method, the method comprising:

acquiring light information from a moving image obtained by imaging a subject using at least one camera with light for each wavelength range of at least three or more of a plurality of wavelength ranges, the light information including at least a luminance intensity for each wavelength range of light in which the moving image is captured;

referring to a light map in which reference light information, which is the light information obtained by measuring light at a plurality of imaging points in advance, is registered for each imaging point of the plurality of imaging points;

instructing movement of the at least one camera to a desired imaging point;

selecting a desired wavelength based on the light information at the desired imaging point at which the moving image is captured; and calculating a heart rate of the subject shown in the moving image based on the selected wavelength.

* * * * *